United States Patent
Bulbrook et al.

(10) Patent No.: US 6,234,169 B1
(45) Date of Patent: May 22, 2001

(54) INHALER

(75) Inventors: Lee Bulbrook, Dereham (GB); Arthur Slutsky, 61 Glen Cedar Road, Toronto, Ontario (CA), M3C 3G4; Noe Zamel, 252 Otonabee Avenue, Willowdale, Ontario (CA), M2M 2T1

(73) Assignees: Arthur Slutsky, Toronto; Noe Zamel, Willowdale, both of (CA)

(*) Notice: Subject to any disclaimer, the term of this patent is extended or adjusted under 35 U.S.C. 154(b) by 0 days.

(21) Appl. No.: 09/134,538

(22) Filed: Aug. 14, 1998

(51) Int. Cl.[7] .................................................. A61M 15/00
(52) U.S. Cl. ................................ 128/203.15; 128/203.12; 604/58
(58) Field of Search .................... 128/203.12, 203.15, 128/203.21, 203.24; 604/58

(56) References Cited

U.S. PATENT DOCUMENTS

| | | | | |
|---|---|---|---|---|
| 263,451 | * | 8/1882 | Adams | 128/203.15 |
| 2,534,636 | * | 12/1950 | Stirn | 128/203.15 |
| 2,549,303 | * | 4/1951 | Friden | 128/203.15 |
| 2,579,280 | * | 12/1951 | Trumbour et al. | 604/58 |
| 2,587,215 | | 2/1952 | Priestly | 128/206 |
| 2,603,216 | * | 7/1952 | Taplin et al. | 128/203.15 |
| 3,938,516 | | 2/1976 | Mathes | 128/266 |
| 3,964,483 | | 6/1976 | Mathes | 128/266 |
| 3,973,566 | | 8/1976 | Mathes | 128/266 |
| 3,980,074 | * | 9/1976 | Watt et al. | 128/203.15 |
| 4,005,711 | | 2/1977 | Glenn | 128/266 |
| 4,014,336 | | 3/1977 | Mathes | 128/266 |
| 4,098,273 | | 7/1978 | Glenn | 128/206 |
| 4,105,027 | * | 8/1978 | Lundquist | 128/203.21 |
| 4,261,354 | | 4/1981 | Nelson | 128/203.23 |
| 4,338,931 | | 7/1982 | Cavazza | 128/203.15 |
| 5,239,993 | | 8/1993 | Evans | 128/203.15 |
| 5,337,740 | | 8/1994 | Armstrong et al. | 128/203.12 |
| 5,441,060 | | 8/1995 | Rose et al. | 131/271 |
| 5,619,985 | | 4/1997 | Ohki et al. | 128/203.21 |
| 5,673,686 | * | 10/1997 | Villax et al. | 128/203.15 |
| 5,683,361 | * | 11/1997 | Elk et al. | 604/58 |
| 5,687,746 | | 11/1997 | Rose et al. | 131/273 |
| 5,690,097 | | 11/1997 | Howard et al. | 128/205.11 |
| 5,702,362 | * | 12/1997 | Harold et al. | 604/58 |

FOREIGN PATENT DOCUMENTS

| | | | | |
|---|---|---|---|---|
| 509878 | * | 2/1955 | (CA) | 128/203.15 |
| 78072 | * | 8/1954 | (DK) | 128/203.15 |
| WO 94/17679 | | 8/1994 | (WO) | A24F/47/00 |

OTHER PUBLICATIONS

Niemi, Eugene E. Jr., The Fluid Mechanics of Cromolyn Sodium Inhalers used for Asthma Prevention, Mar. 22–23, 1979, pp. 33–36, Proceedings of 7th New Eng. (NE) Bioeng. Conf. Troy, NY, U.S.A.

* cited by examiner

Primary Examiner—John G. Weiss
Assistant Examiner—V. Srivastava
(74) Attorney, Agent, or Firm—Bereskin & Parr (57) ABSTRACT

An inhaler for use by an individual to inhale a particulate medicament from a reservoir comprises a chamber having a first end connectable to the reservoir to be in air flow communication therewith, a second end for delivering the medicament to the individual upon inhalation and a conduit defining an air flow path extending between the first end and the second end; and, an orifice in the chamber between the first end and the second end, the orifice utilizing the Coanda Effect when the reservoir is in air flow communication with the chamber and upon inhalation by the individual to draw medicament from the reservoir into the air flow path.

29 Claims, 3 Drawing Sheets

FIG. 3.

INHALER

FIELD OF THE INVENTION

This invention relates to inhalers for powders and other fluids such as a volatile liquid or a gel and more particularly to hand held inhalers for use without medical assistance.

BACKGROUND OF THE INVENTION

The medical community and society in general have been concerned with reducing the hazardous effects of cigarette smoking for many years. The chemicals contained in cigarette smoke produce unwanted effects, including unpleasant odours and health hazards for smokers and bystanders breathing the smoke.

Of the various chemicals contained in cigarette smoke, nicotine is primarily responsible for the pleasurable effects of smoking. Nicotine replacement devices, such as chewing gums or patches, allow a smoker to obtain doses of nicotine without inhaling the other hazardous chemicals in cigarette smoke and without creating smoke that is hazardous to bystanders. Accordingly, nicotine replacement devices may be useful in programs to reduce or eliminate the smokers' dependency on smoking.

Inhaling nicotine as a powder is an effective way to deliver nicotine to the bloodstream. The inhaled powder is deposited on the inner surfaces of the lungs and absorbed into the bloodstream. However, in addition to their desire for nicotine, smokers are also accustomed to the process of smoking. This process includes one or more of the following: handling the cigarettes, tapping the cigarettes against a hard surface before smoking, tapping the cigarette between inhalations to remove ashes and discarding the cigarette when done. Further, smokers are accustomed to inhaling on the cigarette several times to withdraw the nicotine.

Although hand held inhalers, including hand held powder inhalers, for use by a patient without medical assistance currently exist, they have various undesirable features. For example, many devices are designed for medical conditions where a patient requires immediate delivery of a medicament. These devices deliver the medicament in one or, at most, a small number of inhalations. These devices are not suitable for medicaments that are preferably delivered over several inhalations. Further, these devices rely on air currents that flow directly through or across the medicament which causes some of the medicament to travel at high speed and impact the user's airway rather than enter the user's lungs.

Other existing devices rely on complicated or awkward mechanisms for their use. For example, propellers may be used to rotate a capsule to expel powder by centrifugal force, or various rotating or sliding mechanisms may be used to deposit discrete amounts of powder into the airflow path of an inhaler. These devices are complicated and difficult to use discretely. Similarly, many devices require a person to manually insert a medicament container, such as a capsule of powder, into the device in a manner that breaks the container open, again making it difficult to use the device discretely or conveniently. The expense and size of these devices requires them to be reused whereas it would be more convenient and hygienic to make them disposable.

One inhaler of note is Priestly (U.S. Pat. No. 2,587,215). Priestly discloses a device which uses a sliding mechanism to deliver small portions of powder from a remote reservoir to a chamber. The primary airflow enters this chamber and flows through or across the powder. A downstream air inlet provides a secondary airflow that mixes with the primary airflow coming from the chamber to diffuse the powder mixture. To use the device, a person would need to first insert a capsule into the device, and then manipulate the sliding mechanism to put a portion of powder in the chamber for inhalation.

Another inhaler of note is Cavazza (U.S. Pat. No. 4,338,931). Cavazza discloses a device which has two pre-assembled telescoping components which contain a capsule of powder. Each of the two components has a hollow open ended spike which pierces the capsule when the two components are slid together. Air flows into the first spike, through the capsule and through the second spike to a mouthpiece. The device is compact and easily used, but the direct airflow through the powder would deliver most of the powder at high speed in a single inhalation.

Inhalers which comprise a hollow longitudinally extending member are known. For example, Rose et al (U.S. Pat. No. 5,441,060) discloses a hollow cylindrical member wherein the medicament is stored in a thin annular band or in a porous member. According to this patent, air passing longitudinally through the inhaler entrains the medicament. Slutsky et al. (application No. PCT/CA95/0056) also discloses such an inhaler wherein air passing longitudinally through the inhaler entrains the medicament. In these devices, the air passing through the inhaler contacts the medicament as the air travels directly through the inhaler.

SUMMARY OF THE PRESENT INVENTION

In accordance with one embodiment of this invention, there is provided an inhaler for use by an individual to inhale a medicament from a reservoir comprising:

(a) a chamber having a first end connectable to the reservoir to be in air flow communication therewith, a second end for delivering the medicament to the individual upon inhalation and a conduit defining an air flow path extending between the first end and the second end; and, (b) an orifice in the chamber between the first end and the second end, the orifice utilizing the Coanda Effect when the reservoir is in air flow communication with the chamber and upon inhalation by the individual to draw medicament from the reservoir into the air flow path.

In accordance with another embodiment of this invention there is provided an inhaler for use by an individual to inhale a medicament from a reservoir comprising:

(a) a chamber having a first end connectable to the reservoir to be in air flow communication therewith, a second end for delivering the medicament to the individual upon inhalation and a conduit defining an air flow path extending between the first end and the second end;

(b) the conduit including a first portion adjacent the first end, the first portion having an upstream end adjacent the first end and an opposed downstream end, the cross sectional surface area of the first portion decreasing from the downstream end of the first portion to the upstream end of the first portion; and, (c) an orifice positioned between the first end and the second end for introducing undirected air into the chamber upon inhalation by the individual.

The orifice may be positioned in the chamber adjacent the first portion. Alternately, the orifice may be positioned in the first portion. The cross sectional area preferably decreases continuously from the downstream end of the first portion to the upstream end of the first portion. More preferably, the first portion is frusto-conical in shape."

The inhaler may include a seal between the first end and the reservoir when the reservoir is connected to the inhaler, and rupturable by relative movement between the reservoir and the first end.

The inhaler may include a connector which connects the reservoir and the first end of the chamber together when the inhaler is used such that the interior of the reservoir is open to the first end of the chamber but otherwise the reservoir substantially seals the first end of the chamber. The connector may comprise a second portion of the inhaler slidably engaged in relation to the chamber between a first position and a second position, the interior of the reservoir being open to the first end of the chamber in the second position. Alternately, the reservoir may be releasably sealed in the first position and openable by the first end of the reservoir as the second portion is moved from the first position to the second position. In a more preferred embodiment, the reservoir is formed of a folded strip of material sealed at its edges between a closed end and an openable end, the openable end being releasably sealed.

In one embodiment the inhaler resembles a cigarette, the reservoir contains a nicotine formulation and the orifice is located so that the nicotine formulation is withdrawn over a number of inhalations to approximate the nicotine delivery of smoking a cigarette.

In another embodiment, the inhaler further comprises at least one by pass air passage so that the orifice supplies the primary air of inhalation and the by pass passage supplies supplemental air to the reservoir. Preferably, the by pass air passage directs air at the medicament in the reservoir to assist the primary air to remove the medicament from the reservoir.

One advantage of the instant invention is that it provides an inhaler suitable for delivering a dosage of a medicament, preferably a particulate or a powdered medicament, over several inhalations and therefore better simulates the action of smoking. A further advantage is that the inhaler is uncomplicated and simple to use.

One aspect of the present invention involves a device comprising a chamber of increasing cross sectional area. The larger end is connected to a mouthpiece and, in use, the smaller end is open to a reservoir of a medicament to be inhaled. An orifice is preferably provided in the wall of the chamber near but preferably not at the reservoir. It has been found that on inhalation through such a device, air enters the orifice in the chamber and flows to the mouthpiece. There is no primary airflow through or across the medicament (i.e. as the air does passes through the inhaler from the air entry port to the air exit port, it does not travel in a continuous route so as to entrain the medicament). Instead, a portion of the air that enters through the orifice (eg. about half) moves in a direction opposed to the air exit port of the inhaler as it travels towards the reservoir where it entrains a portion of the medicament. The air with the entrained medicament then doubles back to travel to the air exit port of the inhaler. Over several inhalations, all of the medicament may be inhaled.

Another aspect of the present invention involves the manner in which the reservoir of medicament is attached to the device, including the chamber. In one embodiment, the reservoir is formed of a strip of material, folded over and sealed partway along the edges to create a reservoir. The open end of the reservoir may be temporarily sealed to create a cone that fits over the smaller end of the chamber. The loose ends of the strip of material are attached to a second portion of the device that slides relative to the chamber and mouthpiece. The reservoir may be opened simply by sliding the second portion towards the chamber causing the chamber to open the temporary seal and be inserted into the reservoir. It has been found that such a device is easy to use and may be economically produced.

When smokers attempt to stop smoking the recidivism rate is high due to the negative symptoms of withdrawal from nicotine addiction. Replacement therapy with cigarette substitutes is designed to lessen the impact of nicotine withdrawal and to assist a person in withdrawing from cigarette induced nicotine dependency. Cigarette substitutes are suggested as a replacement for cigarettes during the withdrawal period.

Another aspect of the invention is that it can be used to inhale nicotine medicament and preferably a particulate or a powdered nicotine formulation, in a manner similar to smoking a cigarette, cigar or the like. For example, the device may be made of a similar size and appearance as a cigarette. Further, it may be constructed to feel like a cigarette (i.e. it may have a soft feel).

An advantage of the instant invention is that the inhaler may be constructed so as to it may be handled like a cigarette. For example, the inhaler may be constructed so that the nicotine may be delivered over about the same number of inhalations as are required to smoke a cigarette. Thus, the reservoir may contain a single dose of medicament which is equal to the nicotine present in a single cigarette. Further, tapping the device between inhalations may be used to disturb the nicotine powder in the reservoir and enhance the feel of smoking. In particular, multiple inhalations may be required to inhale all of the medicament in the reservoir and it may be tapped between inhalations, as a smoker would tap a cigarette to get rid of ash from the burning end of a cigarette, to loosen some of the medicament in the reservoir so that it will be entrained in the subsequent inhalation.

Such a device may be used as part or all of a smoking cessation or smoking replacement therapy to reduce or eliminate the use of cigarettes, cigars, pipes and the like by an individual. Successful withdrawal from smoking may require the use of the inhaler of the instant invention over a period of time during which inhalers are used to deliver successively smaller nicotine doses until complete withdrawal may be effected. In some cases, such as when a person is unable or unwilling to stop smoking, an inhaler of the instant invention may be used as a permanent tobacco replacement.

In one embodiment a series of inhalers, each having a predetermined dose of a nicotine formulation, are used. Each inhaler is used at time intervals sufficient to reduce the negative effects of nicotine withdrawal.

BRIEF DESCRIPTION OF THE DRAWING FIGURES

For a better understanding of the present invention and to show more clearly how it may be carried into effect, reference will now be made, by way of example, to the accompanying drawings, which show a preferred embodiment of the present invention and in which.

DESCRIPTION OF PREFERRED EMBODIMENT

Figures 1, 2:
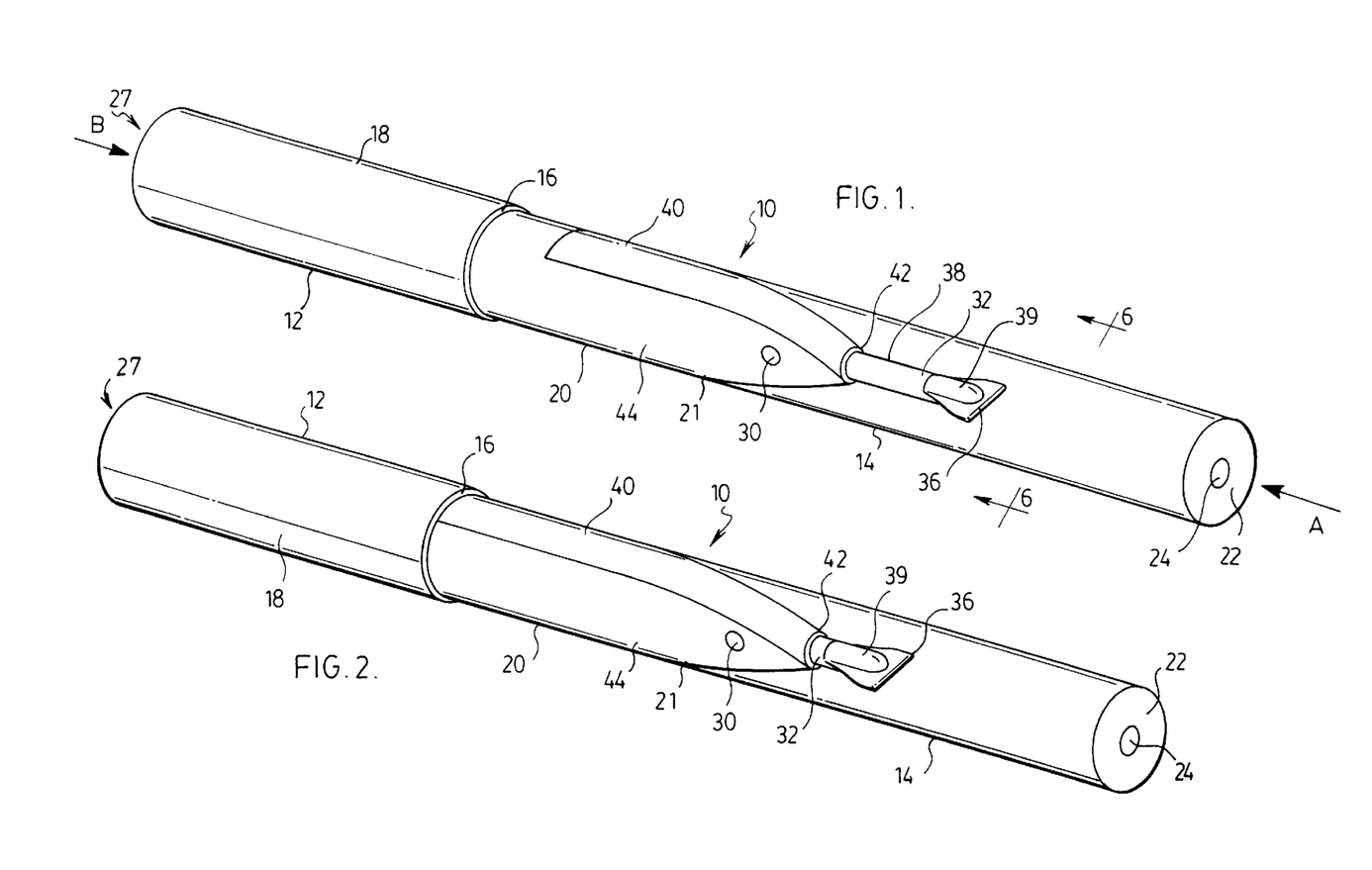
FIG. 1 is a partially sectioned isometric view of the present invention in a first position.
FIG. 2 is a partially sectioned isometric view of the resent invention in a second position.

FIGS. 1 and 2 show the inhaler 10 which comprises a first portion 12 and a second portion 14. First portion 12 includes, and may consist of, a chamber 21 positioned at its upstream end.

Generally, first and second portions 12 and 14 may be of any particular shape and configuration provided chamber 21 is shaped as described herein to produce a reverse flow of air. In the preferred embodiment, both first portion 12 and second portion 14 are generally cylindrical so as to resemble a cigarette or even a cigar and may be made of any suitable material including paper or plastic which are inexpensive and recyclable.

As shown in FIG. 1, first portion 12 has two parts which are separated by an abutment 16. The abutment 16 separates the first portion 12 into a mouthpiece 18 and a plug 20 which has a chamber 21 positioned at its upstream end. Mouthpiece 18 is the downstream exit of inhaler 10 and is configured to deliver the medicament to the oral passageway of the user, and preferably to the mouth of the user. If a shorter inhaler is desired, then the downstream end of plug 20, or even the downstream end of chamber 21, may be used as the mouthpiece.

To increase the resemblance of inhaler 10 to a cigarette, the outer diameter of the mouthpiece 18 is preferably the same as the outer diameter of the second portion 14. Although other sizes or cross sections may also be used, the mouthpiece 18 is also preferably made to resemble the filter portion of a cigarette and the second portion 14 is preferably made to resemble the tobacco portion of a cigarette.

Second portion 14 may be provided merely for aesthetic reasons to cover plug 20. If second portion 14 is made of a structural material, then it may function to provide a protective cover for plug 20. Further, if inhaler 10 is configured to resemble a cigarette or a cigar, then second portion 14 may comprise a longitudinally extending hollow cylinder so that, with mouthpiece 18, inhaler 10 appears to be a single longitudinally extending cylinder. In this embodiment, plug 20 and second portion 14 are configured to lockingly receive second portion 14 in place on plug 20 so that, during use, plug 20 is not accidentally dislodged. To this end, the outer diameter of the plug 20 is preferably substantially the same as the inner diameter of the second portion 14 allowing the second portion 14 to slide on the plug 20 between a first position shown in FIG. 1 and a second position shown in FIG. 2 in which second portion 14 abuts against abutment 16.

Figure 4:
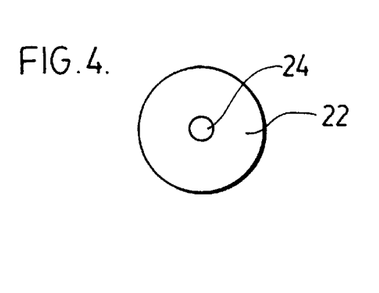
FIG. 4 is an end view in the direction of Arrow A in FIG. 1.
Figure 5:
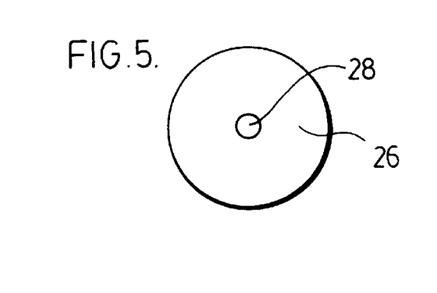
FIG. 5 is an end view in the direction of Arrow B in FIG. 1.

When in use, air flows generally longitudinally through the inhaler 10. The distal end of the second portion 14 may have a cap 22 provided with an inlet 24 that allows air to enter the inhaler 10 (see FIG. 4). Optionally, a filter might be placed in the inlet 24, or the cap 22 sloped inward to act as a baffle if there is some concern about contaminants entering the inhaler 10, or concern that users might try to extract the nicotine in bulk from the inhaler 10. Further, the inclusion of a filter, which may have an exposed face which has the appearance of tobacco would assist inhaler 10 to resemble a cigarette. Similarly, distal end 27 of the mouthpiece 18 may have a plate 26 with an air outlet 28 that allows air to exit the inhaler 10 (see FIG. 5). Again, a filter might be placed in the outlet 28 or the plate 26 angled inwardly to act as a baffle. The inclusion of a filter at distal end 27 would result in inhaler 10 more closely resembling a cigarette. Further, by drawing through a filter, inhaler 10 would better simulate smoking.

Air transfer between first portion 12 and second portion 14 occurs through an orifice 30 in the wall of the first potion 12. Thus, a user inhales through distal end 27 of mouthpiece 18 which creates an area of reduced pressure at the outlet 28 extending throughout the inhaler 10. Air is drawn into the inlet 24, through the second portion 14, through the orifice 30, through the chamber 21, through the remainder of the first portion 12 and into the user's mouth through the outlet 28.

Figure 6:
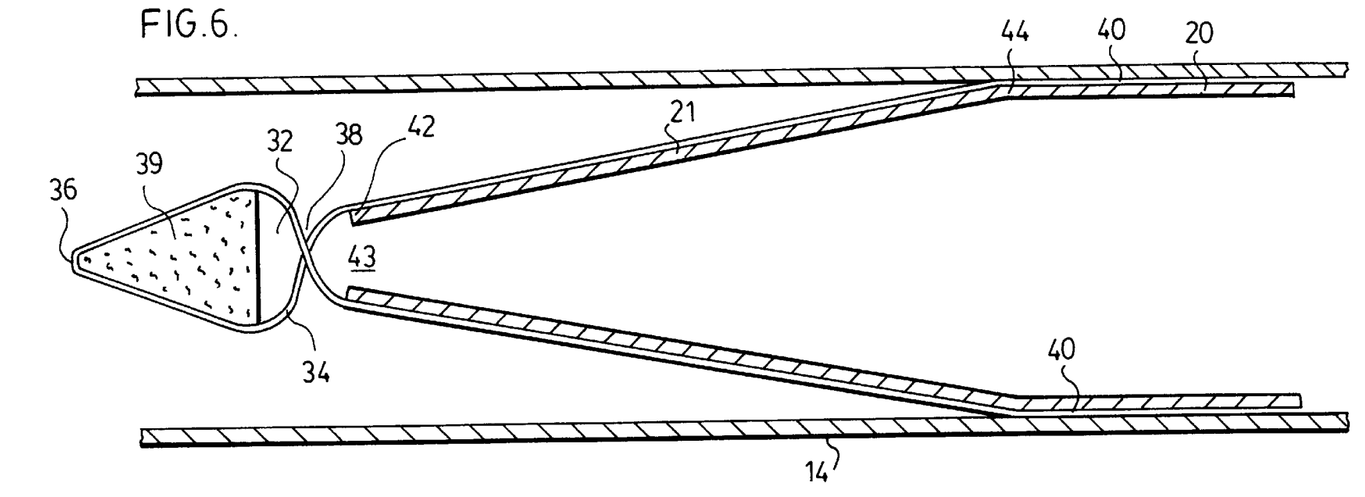
FIG. 6 is a cross-section along the line 6—6 in FIG. 1.

Referring now to FIG. 6, a reservoir 32 is shown in the first position. Reservoir 32 may be of any configuration which is large enough to hold the desired quantity of medicament. The medicament may be any medicament which may be inhaled. For example, the medicament may be a solid (e.g. a powdered medicament or a particulate medicament) or an otherwise fluid medicament (such as a gel or a volatile liquid) wherein a passing airflow through the inhaler can entrain the air directly over the medicament into which some of the medicament has volatilized. Preferably, the medicament is a "solid" medicament comprising individual particles capable of being inhaled.

The solid medicament is preferably a stable powder in a size range suitable for deposition on and absorption across the small airways and the alveolar lining taking into account the amount of water which may be absorbed by the particles as they pass through the lungs. Larger particles, over 5 $\mu$m tend to be deposited in the oral cavity and upper airways, whereas small particles under 0.5 $\mu$m tend to be exhaled from the lung without deposition. The particles grow in size as they are exposed to water in the atmosphere and in the airways of the user. For example, a 0.1 $\mu$m particle may increase to about 0.5 $\mu$m as it passes through the airways to the alveoli and smaller airways of a user. In order to have an appropriate mass, the individual medicament particles, when they exit from the inhaler, may vary in size from about 0.1 $\mu$m to about 5, preferably from about 0.1 $\mu$m to about 3 $\mu$m, more preferably from about 0.1 $\mu$m to about 2 $\mu$m and most preferably from about 0.1 $\mu$m to about 1 $\mu$m. However, it should be noted that the individual particles in the medicament introduced into the inhaler may be aggregated into larger aggregates which are subsequently broken down in the turbulent air flow on inhalation.

The following discussion is premised on the medicament being a "solid". It will be appreciated that the inhaler may also be used with suitable modifications with the other formulations described herein. Reservoir 32 may contain one or a plurality of dosages wherein each dose is preferably removed from reservoir 32 by a plurality of inhalations. Each dose may be in its own individually sealed reservoir 32. If inhaler 10 is configured to resemble a cigarette, then the medicament in reservoir 32 may be a nicotine formulation preferably a solid nicotine formulation and reservoir 32 may be sized so as to receive from about 0.1 to about 5 mg. of nicotine, more preferably from about 0.5 to about 2 mg. of nicotine and, most preferably, the amount of nicotine which is contained in a single cigarette (eg. about 1 mg.). Preferably, reservoir 32 contains a single dose and that dose is equivalent to the amount of nicotine which is contained in a single cigarette. It will be appreciated that reservoir 32 may be relatively large to hold multiple doses of a medicament.

It will also be appreciated that reservoir 32 may be used with a variety of different medicaments. Due to its construction, inhaler 10 preferably requires from about 1 to about 30, more preferably from about 2 to about 15 and, most preferably, from about 3 to about 10 inhalations to withdraw a single dose of medicament from reservoir 32 and transport it into the airways of the user. Therefore, inhaler 10 may be used with any medicament where an entire dose is to be withdrawn slowly. In many cases, the rate at which a medicament is ingested is neutral in terms of the efficacy of the medicament and inhaler 10 may be used with any such medicament.

As will be appreciated by those skilled in the art, if inhaler 10 is not designed to resemble a cigarette, then reservoir 32 may be any medicament storage device known in the industry. For example, reservoir 32 may be a capsule or a bulk medicament dispenser. This will necessitate the inclusion of a device for piercing the capsule so as to expose the medicament in reservoir 32 to airflow through inhaler 10 or to dose a medicament in reservoir 32 into a position where it is within the airstream created by inhaler 10.

In the preferred embodiment, inhaler 10 is configured so as resemble a cigarette, cigar or the like (i.e. a longitudinally extending cylinder) and therefore reservoir 32 is designed to be pierced by a mechanism positioned within section portion 14. Further, reservoir 32 is preferably openable by the external manipulation of inhaler 10 without any obvious controls to activate a piercing mechanism provided on the exterior of inhaler 10 or the need to disassemble inhaler 10 to pierce reservoir 32.

For example, as shown in the Figures, reservoir 32 may be designed to be pierced by a relative motion between reservoir 32 and first portion 12. Reservoir 32 may also be opened by removing a sealing cover such as by peeling off a releasably attached panel. The reservoir 32 may be accordingly formed from a strip 34 of plastic, foil or other material that is substantially impervious to airflow and can be conveniently bonded together. The strip 34 is folded onto itself and the edges sealed together to form the reservoir 32 having a closed end 36 and an openable end 38 and containing the powder 39 to be inhaled. The openable end 38 is temporarily or releasably sealed for example, in a cruciform pattern, in addition to the edge sealing. The edge sealing of the strip 34 ceases shortly after the cruciform pattern of the openable end 38 leaving loose ends 40 which are attached to the inner surface of the second portion 14 in the region of the plug 20. The loose ends 40 thus hold the openable end 38 of the reservoir 32 in close proximity to the chamber 21 in the first position. The device can be stored or transported in this first position without spilling the powder 39 from the reservoir 32.

As shown in FIG. 6, chamber 21 extends between a first end 42 and a second end 44. Second end 44 is provided at the junction of chamber 21 and plug 20. First end 42 defines an opening 43 which is positioned so as to draw medicament from reservoir 32. Reservoir 32 is preferably positioned adjacent opening 43. Opening 43 is relatively small. Opening 43 is preferably circular in shape and may have a diameter from about 3 mm to about 0.5 mm, more preferably from about 2 mm to about 1 mm, and most preferably about 1.5 mm.

Orifice 30 may be positioned at an intermediate point along plug 20 or chamber 21. Orifice 30 may be positioned on plug 20 adjacent second end 44, or preferably, orifice 30 is positioned in chamber 21 between second end 44 and first end 42. The closer orifice 30 is positioned to opening 43, the greater the amount of medicament which will be withdrawn from reservoir 32 upon each inhalation. Accordingly, in order to increase the efficiency of inhaler 10, orifice 30 is positioned closer to opening 43. In order to better simulate cigarette smoking, orifice 30 may be positioned at an intermediate position between first and second ends 42 and 44 so that a number of inhalations will be required to withdraw a full dose of medicament from reservoir 32.

Chamber 21 is configured so that the cross-sectional area of first end 42 is less than the cross-sectional area of second end 44. Preferably, as shown in FIG. 6, the cross-sectional area continually diminishes from second end 44 to first end 42. More preferably, the cross-sectional area decreases at a constant rate from second end 44 to first end 42. The cross-sectional shape of chamber 21 may be of an particular geometric configuration. For example, chamber 21 may be circular, square or triangular in cross-section. In the preferred embodiment, chamber 21 is frusto-conical in shape. The first end may have a diameter of approximately 15 mm and chamber 21 may taper at approximately 20 degrees. Such a chamber is both effective and easily produced although chambers of other shapes or dimensions are workable. In particular, a chamber 21 having decreasing cross sectional area near the first end 42 only is operable. The taper of the first end 42 of the chamber 21 preferably approximates that of the openable end 38 of the reservoir 32.

To use the inhaler, reservoir 32 must be brought into air flow communication with first end 42. To do this, the user may slide the second portion 14 relative to the first portion 12 from the first position (FIG. 1) to the second position (FIG. 2), such as by tapping the inhaler 10 on a hard surface. The movement between the first and second positions may be about 5 mm and results in the inhaler 10 being configured as shown in FIG. 2. As the second portion 14 is moved to the second position, the chamber 21 advances through the temporary seal of the openable end 38 of the reservoir 32. In the resulting second position, it is preferred that reservoir 32 have sealed edges which surround and substantially seal, and preferably completely seal, the first end 42 of the chamber 21. Thus, in the second position, air and powder 39 can travel to or from the reservoir 32 via opening 43.

Reservoir 32 need not provide an absolute airtight seal around the first end 42 of the chamber 21, but any leaks should not entrain an appreciable amount of powder 39 and transport it into the chamber 21. Inhaler 10 will function with secondary air entering reservoir 32 directly from second portion 14 without travelling through chamber 21. For example, any leaks in the airtight seal between first end 42 and reservoir 32 may permit up to, for example, about 5 percent of the air inhaled by a user to travel directly into reservoir 32. Such air is preferably directed at the surface of medicament 39 so as to break up or deconsolidate the medicament in reservoir 32. The loosened material resulting from this process becomes more readily drawn into chamber 21 though the action of the primary air entering through orifice 30. Chamber 21 may be designed, such as by providing one or more grooves 45 on the outer surface of chamber 21 so as to direct jets of air at the surface of medicament 39.

Upon inhalation, powder 39 is drawn from the reservoir 32 through the opening 43 of the chamber 21 primarily by air currents (or entirely if there are no leaks or grooves 45) originating in the chamber 21. If desired, the inhaler 10 could also be adapted to use a standard pharmaceutical capsule as the reservoir 32. For example, the capsule could be held in fixed relation to the second portion 14 and the first end 42 of the chamber 21 adapted to pierce the capsule when the second portion 14 is moved to the second position (not shown).

Figure 3:
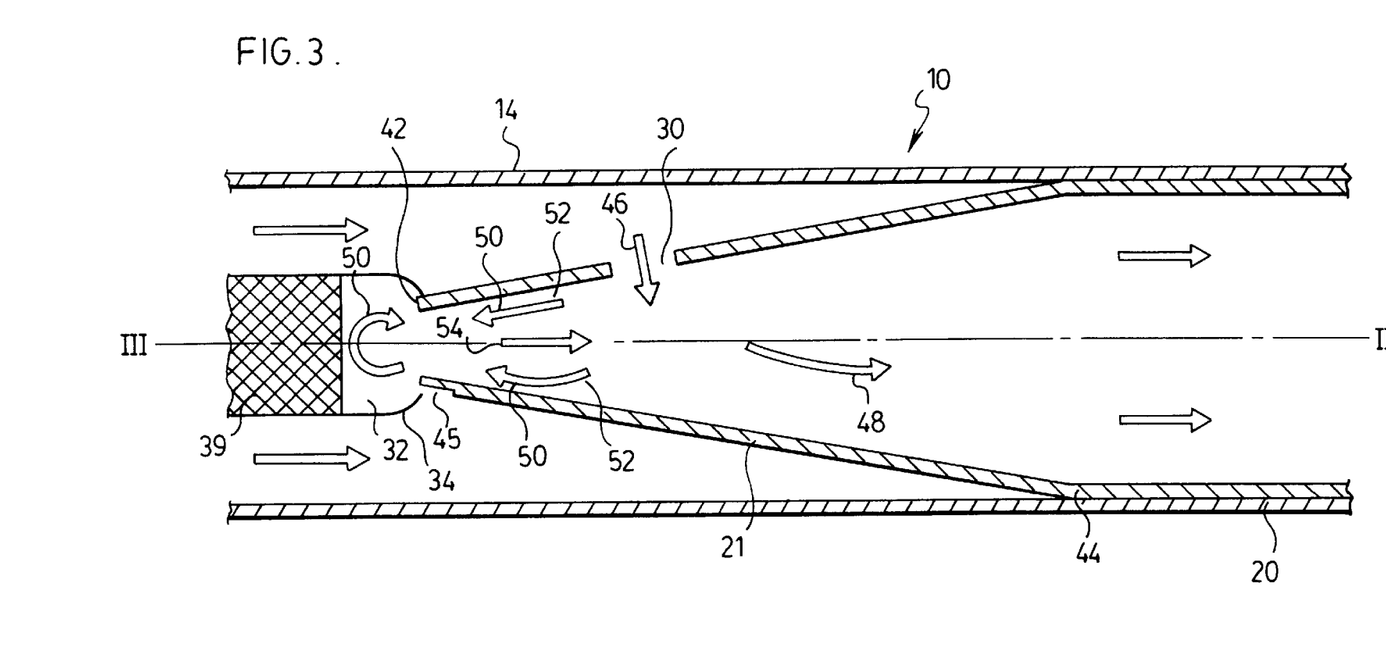
FIG. 3 is a sectional view of a portion of the invention along line III—III in FIG. 2.

Referring now to FIG. 3, a portion of the inhaler 10 is shown in the second position. As discussed above, a person inhaling on the inhaler 10 draws air through the second portion 14 which flows through the orifice 30 and into the chamber 21. The movement of air through the inhaler 10 is most restricted at the orifice 30. For example, orifice 30 may be circular and may have a diameter from about 4 mm to about 1 mm, more preferably from about 3 mm to about 1.5, and most preferably about 2 mm in diameter. Further, an inhaler may be provided with more than one orifice 30. Because of the restriction in cross sectional area of airflow at the orifice 30, the air travels quickly in the area of the orifice 30 creating an inflow jet 46. Orifice 30 is shaped and configured so as to direct air into chamber 21 in an undirected fashion. For example, orifice 30 is provided in the side wall of chamber 21 without any baffles or other deviation in the wall surrounding orifice 30 so as to direct air either towards first end 42 or second end 44. Accordingly, inflow jet 46 travels inwardly into chamber 21 along an axis which is substantially transverse to the wall of chamber 21 adjacent orifice 30.

A portion of the air entering via inflow jet 46 flows towards the second end 44 of the chamber 21 (primary airflow 48). This air is drawn towards the vacuum created by the person inhaling on the inhaler 10. The other portion of the air flow (secondary airflow 50) flows towards the first end 42 of the chamber 21 and into the reservoir 32 before travelling through chamber 21 to distal end 27. As shown in FIG. 3, the secondary airflow 50 travels rearwardly to reservoir 32 (delivery branch 52) and then scours the surface of the powder 39 in the reservoir 32 and entrains a small portion of the powder 39. A return branch 54 of the secondary airflow 50 then flows back towards the second end 44 of the chamber 21 to a point where at least some and preferably all of it, mixes with the primary airflow 48. Powder 39 is entrained in the return branch 54 of the secondary airflow 50 as it mixes with the primary airflow 48 and is carried through the inhaler 10 with the primary airflow 48 to the user. Because of dilution, the concentration of powder 39 in the primary airflow 48 is significantly less than the concentration of powder 39 in the secondary airflow 50.

When air is drawn through inhaler 10, a pressure differential is set up in inhaler 10. The focal point of this pressure differential is across orifice 30 in chamber 21. Upon inhalation, the air pressure inside chamber 21 is reduced and consequently, the air entering orifice 30 has a higher static pressure. It is believed that the effectiveness of inhaler 10 is assisted by the Coanda Effect whereby a stream of quickly moving air tends to travels along a nearby surface. Pursuant to the Coanda Effect, when a stream of gas at a given pressure is introduced to a gas at a lower pressure, the higher pressure gas will tend to stick to the nearest solid object. This creates a resultant negative pressure zone inwards of the nearest solid object. Without being limited by theory, referring to FIG. 3, as incoming air jet 46 enters chamber 21 via orifice 30, a portion of the air travels along the decreasing cross-sectional area of chamber 21 towards opening 43 (deliver branch 52). A negative air pressure is created centrally within chamber 21 along axis III—III. This provides a low pressure zone for the air exiting reservoir 32 to travel towards distal end 27 of inhaler 10 (return branch 54). It is believed that the air entering orifice 30 has virtually no depth in which to produce a laminar flow component. Therefore, deliver branch 52 is turbulent in nature.

Due to the Coanda Effect, the tendency is for approximately half of the air entering orifice 30 to try and travel to opening 43 of chamber 21. As the cross-sectional area of chamber 21 diminishes, the local air velocity pressure component increases and is matched by a decrease in static pressure. The drop in static pressure further encourages delivery branch 52 to travel in a reverse flow towards opening 43. Thus, the resultant turbulent nature of the air adjacent to opening 43 is sufficient to entrain some of the powder 39. Since the dominant effect is to force air through inhaler 10 to distal end 27, a portion of the captured content of power 39 is turbulently drawn into first portion 12 and then out through mouthpiece 18.

As well as entraining powder 39, the turbulent airflow also has a consolidating effect on power 39 in reservoir 32. This limits the amount of medicament which may be drawn up into chamber 21 with any particular inhalation. If a small secondary air supply is provided (e.g. a pair of opposed grooves 45) bypass air jets may be provided which are sufficient to just disrupt the surface of powder 39 within reservoir 32. The portion of disrupted powder 39 at the air/medicament interface is caught up in the turbulent airflow and eventually leaves reservoir 32.

As an alternative (or in addition) to introducing side air jets directed at powder 39, it is also possible to simply agitate inhaler 10. For example, if the device is tapped or flicked (similar to the action which would be required to dislodge ash from a burning cigarette) the surface of powder 39 can be encouraged to deconsolidate. The loosened material resulting from this process becomes more readily caught up in the turbulent air inside reservoir 32, which scours out the predominantly empty volume of reservoir 32.

The location of the orifice 30 can be altered to increase or decrease the effectiveness of the secondary airflow 50 in removing powder 39 from the reservoir 32. Moving the orifice 30 to a position adjacent the second end 44 will reduce the amount of powder 39 inhaled with each inhalation. Similarly, moving the orifice 30 towards the first end 42 generally increases the amount of powder 39 drawn in with each inhalation. In a preferred embodiment for use as a device for inhaling nicotine as a replacement for smoking, an amount of nicotine similar to that inhaled from a regular cigarette would be inhaled in 5 to 10 inhalations.

The descriptions of airflow patterns given above have been simplified or idealized for assistance in understanding the invention. For example, it is likely that flows throughout the inhaler 10 are turbulent and may contain components of flows in many directions. Further, the use of FIG. 3 is not intended to imply that the airflows in the inhaler 10 move in a plane. Nor is it necessary for the working of the invention that the secondary airflow 50 be exactly as shown provided that a secondary airflow 50 capable of entraining the powder 39 is created.

We claim:

1. An inhaler for use by an individual to inhale a medicament from a reservoir comprising:

(a) a chamber having a conduit having a first end connectable to the reservoir to be in air flow communication therewith and a second end for delivering the medicament to the individual upon inhalation, the conduit defining an air flow path extending between the first end and the second end; and, (b) an orifice in the chamber for entry of air into the conduit between the first end and the second end, the orifice and the conduit configured to produce in air entering the conduit through the orifice a Coanda Effect whereby air entering the conduit via the orifice travels to the reservoir to draw medicament from the reservoir into the air flow path when the reservoir is in air flow communication with the chamber and upon inhalation by the individual.

2. The inhaler as claimed in claim 1 further comprising a seal between the first end and the reservoir when the reservoir is connected to the inhaler, and rupturable by relative movement between the reservoir and the first end.

3. The inhaler as claimed in claim 1 further comprising a connector which connects the reservoir and the first end of the chamber together when the inhaler is used such that the interior of the reservoir is open to the first end of the chamber but otherwise the reservoir substantially seals the first end of the chamber.

4. The inhaler of claim 3 wherein the connector comprises a second portion of the inhaler slidably engaged in relation to the conduit between a first position and a second position, the interior of the reservoir open to the first end of the conduit in the second position.

5. The inhaler of claim 4 wherein the reservoir is releasably sealed in the first position and openable by the first end of the reservoir as the second portion is moved from the first position to the second position.

6. The inhaler of claim 4 wherein the reservoir is formed of a folded strip of material sealed at its edges between a closed end and an openable end, the openable end releasably sealed.

7. The inhaler of claim 1 wherein the inhaler resembles a cigarette, the reservoir contains a nicotine formulation and the orifice is located so that the nicotine formulation is withdrawn over a number of inhalations to approximate the nicotine delivery of smoking a cigarette.

8. The inhaler of claim 1 further comprising at least one by pass air passage so that the orifice supplies the primary air of inhalation and the by pass passage supplies supplemental air to the reservoir.

9. The inhaler of claim 8 wherein the by pass air passage directs air at the medicament in the reservoir to assist the primary air to remove the medicament from the reservoir.

10. The inhaler of claim 1 wherein the medicament is a solid medicament.

11. An inhaler for use by an individual to inhale a medicament from a reservoir comprising:
   (a) a chamber having a conduit having a first end connectable to the reservoir to be in air flow communication therewith and a second end for delivering the medicament to the individual upon inhalation the conduit defining an air flow path extending between the first end and the second end;
   (b) the conduit including a first portion adjacent the first end, the first portion having an upstream end adjacent the first end and an opposed downstream end, the cross sectional surface area of the first portion decreasing from the downstream end of the first portion to the upstream end of the first portion; and,
   (c) an orifice positioned between the first end and the second end for introducing undirected air into the conduit upon inhalation by the individual whereby the configuration of the orifice and the conduit produce a Coanda Effect upon inhalation.

12. The inhaler as claimed in claim 11 wherein the orifice is positioned in the chamber adjacent the first portion.

13. The inhaler as claimed in claim 11 wherein the orifice is positioned in the first portion.

14. The inhaler as claimed in claim 13 wherein the cross sectional area decreases continuously from the downstream end of the first portion to the upstream end of the first portion.

15. The inhaler as claimed in claim 13 wherein the first portion is frusto-conical in shape.

16. The inhaler as claimed in claim 11 further comprising a seal between the first end and the reservoir when the reservoir is connected to the inhaler, and rupturable by relative movement between the reservoir and the first end.

17. The inhaler as claimed in claim 11 further comprising a connector which connects the reservoir and the first end of the chamber together when the inhaler is used such that the interior of the reservoir is open to the first end of the chamber but otherwise the reservoir substantially seals the first end of the chamber.

18. The inhaler of claim 17 wherein the connector comprises a second portion of the inhaler slidably engaged in relation to the chamber between a first position and a second position, the interior of the reservoir being open to the first end of the chamber in the second position.

19. The inhaler of claim 17 wherein the reservoir is releasably sealed in the first position and openable by the first end of the reservoir as the second portion is moved from the first position to the second position.

20. The inhaler of claim 17 wherein the reservoir is formed of a folded strip of material sealed at its edges between a closed end and an openable end, the openable end being releasably sealed.

21. The inhaler of claim 11 wherein the inhaler resembles a cigarette, the reservoir contains a nicotine formulation and the orifice is located so that the nicotine formulation is withdrawn over a number of inhalations to approximate the nicotine delivery of smoking a cigarette.

22. The inhaler of claim 11 further comprising at least one by pass air passage so that the orifice supplies the primary air of inhalation and the by pass passage supplies supplemental air to the reservoir.

23. The inhaler of claim 22 wherein the by pass air passage directs air at the medicament in the reservoir to assist the primary air to remove the medicament from the reservoir.

24. The inhaler of claim 11 wherein the medicament is a solid medicament.

25. A method of providing nicotine to supply a person's tobacco smoking induced nicotine dependency comprising inhaling a predetermined dose of a medicament comprising at least one nicotine formulation suitable for absorption into the bloodstream of the person from an inhaler having:
   (a) a chamber having a conduit having a first end connectable to the reservoir to be in air flow communication therewith and a second end for delivering the medicament to the individual upon inhalation, the conduit defining an air flow path extending between the first end and the second end; and,
   (b) an orifice in the chamber for air entry to the conduit between the first end and the second end, the orifice and the conduit configured to produce in air entering the conduit through the orifice a Coanda Effect when the reservoir is in air flow communication with the chamber and upon inhalation by the individual to draw medicament from the reservoir into the air flow path wherein the inhaler is used by the person as a tobacco substitute and the chamber configured to produce in air entering the conduit through the orifice a Coanda Effect whereby air entering the conduit via the orifice travels to the reservoir to draw medicament from the reservoir into the air flow path.

26. A method as claimed in claim 25 wherein said method is repeated at time intervals sufficient to reduce the negative effects of nicotine withdrawal.

27. A method as claimed in claim 25 wherein the introduction of the predetermined dose is used as a tobacco substitute.

28. A method as claimed in claim 25 wherein the introduction of the predetermined dose is used to assist the person to withdraw from nicotine dependency.

29. A method as claimed in claim 25 wherein the person taps the inhaler between inhalations to mechanically assist the entrainment of the nicotine formulation in the air passing through the inhaler.

* * * * *